United States Patent [19]
Rabkin et al.

[11] Patent Number: 5,917,013
[45] Date of Patent: Jun. 29, 1999

[54] PEPTIDES AND THEIR USE TO AMELIORATE CELL DEATH

[75] Inventors: Simon W. Rabkin; Gerald Krystal, both of Vancouver, Canada

[73] Assignee: Simon W. Rabkin, Vancouver, Canada

[21] Appl. No.: 08/759,599

[22] Filed: Dec. 5, 1996

Related U.S. Application Data

[60] Provisional application No. 60/008,233, Dec. 6, 1995.

[51] Int. Cl.$^6$ .............................. C07H 21/00; C07K 7/06; C07K 7/08; C07K 14/00

[52] U.S. Cl. ........................... 530/300; 530/326; 530/327; 530/329; 536/23.1

[58] Field of Search .................................. 514/2, 13, 14, 514/15, 16, 17, 44; 530/300, 326, 327, 328, 329; 536/23.1, 23.2, 23.7

*Primary Examiner*—Nancy Degen
*Assistant Examiner*—Robert Schwartzman
*Attorney, Agent, or Firm*—Seed and Berry LLP

[57] ABSTRACT

There is disclosed novel peptides, fragments or analogues thereof and polynucleotides encoding the same, derived from streptokinase suitable for use in the amelioration of cell death and methods related thereto.

10 Claims, 3 Drawing Sheets

IAGPEWLLDR PSVNNSQLVV SVAGTVGTN QDISLKFFEI DLTSRPAHGG
KTEQGLSPKS KPFATDSGAM SHKLEKADLL KAIQEQLIAN VHSNDDYFEV
IDFASDATIT DRNGKVYFAD KDGSVTLPTQ PVQEFLLSGH VRVRPYKEKP
IQNQAKSVDV EYTVQFTPLN PDDDFRPGLK LTKLLKTLAI GDTITSQELL
AQAQSILNKN HPGYTIYERD SSIVTHDNDI FRTILPMDQE FTYRVKNREQ
AYRINKKSGL NEEINNTDLI SLEYKYVLKK GEKPYDPFDR SHLKLFTIKY
VDVDTNELLK SEQLLTASER NLDFRDLYDP RDKAKLLYNN LDAFGIMDYT
LTGKVEDNHD DTNRIITVYM GKRPEGENAS YHAYDKDRY TEEEREVYSY
LRYTGTPIPD NPDDK (SEQ. ID. No. 12)

FIG. 3

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Ser Val Asp Val Glu Tyr
1               5

(2) INFORMATION FOR SEQ ID NO:2:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Tyr Val Asp Val Asp Thr
1               5

(2) INFORMATION FOR SEQ ID NO:3:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Thr Val Asp Val Glu Tyr
1               5

(2) INFORMATION FOR SEQ ID NO:4:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:4:

Tyr Val Asp Val Asp Thr Asn Glu Leu Leu Lys
1               5                   10

(2) INFORMATION FOR SEQ ID NO:5:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:5:

Ser Val Asp Val Glu Tyr Thr Val Gln Phe Thr Pro Leu Asn Pro Asp
1               5                  10                  15

Asp Asp (2) INFORMATION FOR SEQ ID NO:6:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Ser Val Asp Val Glu Tyr Thr Gln Phe Thr Asp Phe Arg Gly Lys Leu
1               5                  10                  15

Thr Lys Leu Leu
            20

(2) INFORMATION FOR SEQ ID NO:7:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Ser Val Asp Val Glu Tyr Thr Val Gln Phe Thr Pro Leu Asn Pro Asp
1               5                  10                  15

Asp Asp Phe Arg Pro
            20

(2) INFORMATION FOR SEQ ID NO:8:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Tyr Val Asp Val Asp Thr Asn Glu Leu Leu Lys Ser Glu Gln Leu Leu
1               5                  10                  15

Thr Ala Ser Glu
            20

(2) INFORMATION FOR SEQ ID NO:9:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

```
Asn Phe Leu Arg Gly Lys Leu Lys Leu Tyr Thr Gly Glu Ala Cys Arg
1               5                   10                  15

Thr Gly Asp Arg
            20
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:10:

```
Arg Leu Ile Leu Asp Ser Arg Val Leu
1               5

Glu Arg Tyr Leu Leu Glu Ala Lys Glu Ala Glu
10                  15                  20
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:11:

```
Glu Val Thr Glu Glu Glu Glu Thr Val Pro Leu Lys Thr Leu Glu Ala
1               5                   10                  15

Met Ile Asp Glu
            20
```

(2) INFORMATION FOR SEQ ID NO:12:

(i) SEQUENCE CHARACTERISTICS:
        (A) LENGTH: 413 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:12:

```
Ile Ala Gly Pro Glu Trp Leu Leu Asp Arg Pro Ser Val Asn Asn Ser
1               5                   10                  15

Gln Leu Val Val Ser Val Ala Gly Thr Val Gly Thr Asn Gln Asp Ile
                20                  25                  30

Ser Leu Lys Phe Phe Glu Ile Asp Leu Thr Ser Arg Pro Ala His Gly
            35                  40                  45

Gly Lys Thr Glu Gln Gly Leu Ser Pro Lys Ser Lys Pro Phe Ala Thr
        50                  55                  60

Asp Ser Gly Ala Met Ser His Lys Leu Glu Lys Ala Asp Leu Leu Lys
65                  70                  75                  80

Ala Ile Gln Glu Gln Leu Ile Ala Asn Val His Ser Asn Asp Asp Tyr
                85                  90                  95

Phe Glu Val Ile Asp Phe Ala Ser Asp Ala Thr Ile Thr Asp Arg Asn
                100                 105                 110

Gly Lys Val Tyr Phe Ala Asp Lys Asp Gly Ser Val Thr Leu Pro Thr
            115                 120                 125
```

```
Gln Pro Val Gln Glu Phe Leu Leu Ser Gly His Val Arg Val Arg Pro
    130                 135                 140
Tyr Lys Glu Lys Pro Ile Gln Asn Gln Ala Lys Ser Val Asp Val Glu
145             150                 155                     160
Tyr Thr Val Gln Phe Thr Pro Leu Asn Pro Asp Asp Phe Arg Pro
                165                 170             175
Gly Leu Lys Leu Thr Lys Leu Leu Lys Thr Leu Ala Ile Gly Asp Thr
            180                 185                 190
Ile Thr Ser Gln Glu Leu Leu Ala Gln Ala Gln Ser Ile Leu Asn Lys
        195                 200                 205
Asn His Pro Gly Tyr Thr Ile Tyr Glu Arg Asp Ser Ser Ile Val Thr
        210             215                 220
His Asp Asn Asp Ile Phe Arg Thr Ile Leu Pro Met Asp Gln Glu Phe
225                 230                 235                 240
Thr Tyr Arg Val Lys Asn Arg Glu Gln Ala Tyr Arg Ile Asn Lys Lys
                245                 250                 255
Ser Gly Leu Asn Glu Glu Ile Asn Asn Thr Asp Leu Ile Ser Leu Glu
            260                 265                 270
Tyr Lys Tyr Val Leu Lys Lys Gly Glu Lys Pro Tyr Asp Pro Phe Asp
        275                 280                 285
Arg Ser His Leu Lys Leu Phe Thr Ile Lys Tyr Val Asp Val Asp Thr
        290                 295                 300
Asn Glu Leu Leu Lys Ser Glu Gln Leu Leu Thr Ala Ser Glu Arg Asn
305                 310                 315                 320
Leu Asp Phe Arg Asp Leu Tyr Asp Pro Arg Asp Lys Ala Lys Leu Leu
                325                 330                 335
Tyr Asn Asn Leu Asp Ala Phe Gly Ile Met Asp Tyr Thr Leu Thr Gly
            340                 345                 350
Lys Val Glu Asp Asn His Asp Asp Thr Asn Arg Ile Ile Thr Val Tyr
            355                 360                 365
Met Gly Lys Arg Pro Glu Gly Glu Asn Ala Ser Tyr His Ala Tyr Asp
    370                 375                 380
Lys Asp Arg Tyr Thr Glu Glu Glu Arg Glu Val Tyr Ser Tyr Leu Arg
385                 390                 395                 400
Tyr Thr Gly Thr Pro Ile Pro Asp Asn Pro Asp Asp Lys
                405                 410
```

PEPTIDES AND THEIR USE TO AMELIORATE CELL DEATH

CROSS-REFERENCE TO RELATED APPLICATION

This application claims the benefit of provisional Application No. 60/008,233, filed Dec. 6, 1995.

TECHNICAL FIELD

The present invention generally relates to novel compositions and methods for use thereof in the amelioration of cell death. More specifically, the present invention is directed to a series of peptides derived from streptokinase and their use in the amelioration of apoptosis and/or necrosis.

BACKGROUND OF THE INVENTION

Cell death occurs in both normal human development and in pathological conditions. Two kinds of cell death have been recognized: apoptosis and necrosis. Briefly, apoptosis, or programmed cell death, is a natural process that is triggered by specific biological events and proceeds by well-defined mechanisms. Apoptosis occurs by compaction and convolution of the nuclear chromatin into dense masses, fragmentation of the nucleus, and blebbing of the plasma membrane, ultimately resulting in cell death. Even though 50% of an organism's cells are experiencing some stage of apoptosis at any given time, the process is observable in only about 0.1% of those cells.

Necrosis, on the other hand, is easily observed. Necrosis results from severe or sudden insult, for example as a result of physical trauma, anoxia, hyperthermia or chemically induced damage. Briefly, necrosis is typified by early changes in the structure and function of the mitochondria. When the mitochondria are unable to provide energy to the cell, the cell can no longer maintain homeostasis. The plasma membrane then loses its ability to regulate osmotic pressure and the cell swells and bursts, spilling its contents into the surrounding tissue and provoking an inflammatory response. In cases of severe injury or bacterial infection, this response can result in additional tissue damage. Cell necrosis is associated with diseases that result from the acute interruption of blood flow to any organ of the body. For example, the interruption of blood flow to the heart, brain, or kidney may produce, by way of example, myocardial infarction, cerebral infarction, or renal infarction, respectively. Cell necrosis is also associated with the toxic effects of bacteria and chemicals and bacterial or viral infections of any organ in the body.

Apoptosis appears to be genetically regulated. However, apoptosis can be induced by exposing cells to radiation, heat, cytotoxic agents, and abnormal changes in cellular biology. Excessive cell death may result in crippling degenerative disorders, for example, the annihilation of vital $CD4^+$ T-lymphocytes in HIV infected patients; the elimination of neurons, and other cell types, following ischemia and reperfusion; and the destruction of cells after exposure to ionizing or ultraviolet radiation in the treatment of neoplastic disorders. These disorders are thought to stem from ectopically programmed cell death, i.e., metabolic or infective factors that induce the apoptosis. Too little cell death can result in proliferative disorders, such as neoplastic disorders or autoimmune disease when a particular immune cell lives beyond its appropriate life span.

One common trigger of apoptosis in the acquisition of these disorders is oxidative stress, which causes the production of free radicals. Free radicals are highly reactive molecular species which interact with a wide variety of naturally occurring cellular components. Exposure to free radical leads to cumulative damage to cellular components and, ultimately, to the tissue itself.

A variety of factors may increase the free radical concentration and oxidative stress, thereby rendering the warm-blooded animal susceptible to cell death and its associated disorders. Such factors include considerations of genetics, nutritional status, exposure to drug therapy, drug metabolism, disease, and environmental factors. A change in any one of these factors may result in a failure of the body's defensive mechanisms and lead to cell death. Cellular damage has been invoked as a possible etiology in the development of various degenerative disorders, including, by way of example, cardiovascular disease, autoimmune disorders, arthritis, cancer, pancreatitis, hepatoxicity, cataracts, macular degeneration, accelerated aging, Parkinson's disease, Alzheimer's disease, and the like.

The present invention discloses novel compositions and methods for the amelioration of cell death, and further provides other related advantages.

SUMMARY OF THE INVENTION

As noted above, the present invention provides compositions and methods for the amelioration of cell death due to necrosis or apoptosis.

One aspect of the present invention is compositions, comprising peptides, and fragments or analogues thereof, derived from streptokinase and capable of ameliorating cell death.

Another aspect of the present invention is an isolated nucleic acid segment, comprising a polynucleotide encoding a peptide, or a fragment or analogue thereof, derived from streptokinase and the peptide being capable of ameliorating cell death.

Another aspect of the present invention is a pharmaceutical composition, comprising a compound, as disclosed above, in a suitable pharmaceutical excipient or diluent.

Another aspect of the present invention is a method of ameliorating cell death, comprising treating a warm-blooded animal by administering a therapeutically effective amount of a compound, as described above, such that cell death is ameliorated. In one embodiment of this aspect, the warm-blooded animal is suffering from a disorder selected from the group consisting of neurodegenerative disorders, cardiovascular diseases, immune diseases, neoplastic disorders, inflammatory disorders, myelodegenerative disease, viral disease and degenerative diseases of any organ.

Neurodegenerative disorders include, by way of example, Parkinson's, Alzheimer's, Huntington's, cerebellar degeneration, and FALS.

Cardiovascular diseases include, by way of example, hypertensive heart disease, heart failure, atherosclerosis, myocardial infarction, and myocardial reperfusion injury.

Immune diseases include, by way of example, autoimmune disease, AIDS/HIV, and immune deficiencies. Autoimmune diseases include, by way of example, rheumatoid arthritis, systemic lupus erythematosus, insulin-dependent diabetes mellitus, myasthenia gravis, glomerulonephritis, lupus, pernicious anemia, dermatomyositis, enythema nodosum, Sjögren's syndrome, temporal arteritis, Wegener's granulomatosis, antiphospholipid syndrome, and autoimmune polyarthritides.

Neoplastic disorders include, by way of example, leukemia, sarcomas, myelomas, carcinomas, neuromas, melanoma, cancers of the breast, brain, colon, cervix, or prostrate, Hodgkin's disease, and non-Hodgkin's lymphoma.

Inflammatory diseases include, by way of example, inflammatory joint disorders, arthritis, and inflammatory-induced cell damage to eye, brain, and other organs. Viral diseases include, by way of example, viral infections, such as hepatitis, retroviral infections, and viral encephalitis. Other disorders include macular degeneration, cataracts, pancreatitis, Crohn's disease, ulcerative colitis, and accelerated aging.

In another aspect of the present invention, the warm-blooded animal is suffering from an insult selected from the group consisting of physical trauma, anoxia, hyperthermia, chemically-induced damage, and radiation-induced damage.

In still yet another aspect of the present invention, the warm-blooded animal has been subjected to a procedure selected from the group consisting of bypass surgery, chemotherapy, and organ transplantation.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety as if each were explicitly incorporated herein.

DETAILED DESCRIPTION OF THE INVENTION

As noted above, the present invention generally relates to novel compositions and the use thereof in methods of ameliorating cell death. Specifically, the present invention pertains to novel peptides derived from streptokinase and a method of use thereof to ameliorate apoptosis or necrosis.

Within the context of the present invention, the term "cell death" refers to apoptosis or necrosis. The term "apoptosis" refers to programmed cell death. The term "necrosis" refers to cell death as a response to overwhelming cellular or tissue injury. The term "ameliorate" or "amelioration" refers to an inhibition of cell death such that the incidence of cell death is generally decreased by 50%–80%, typically decreased by greater than 80% and, preferably, decreased by greater than 95%.

Figure 3:
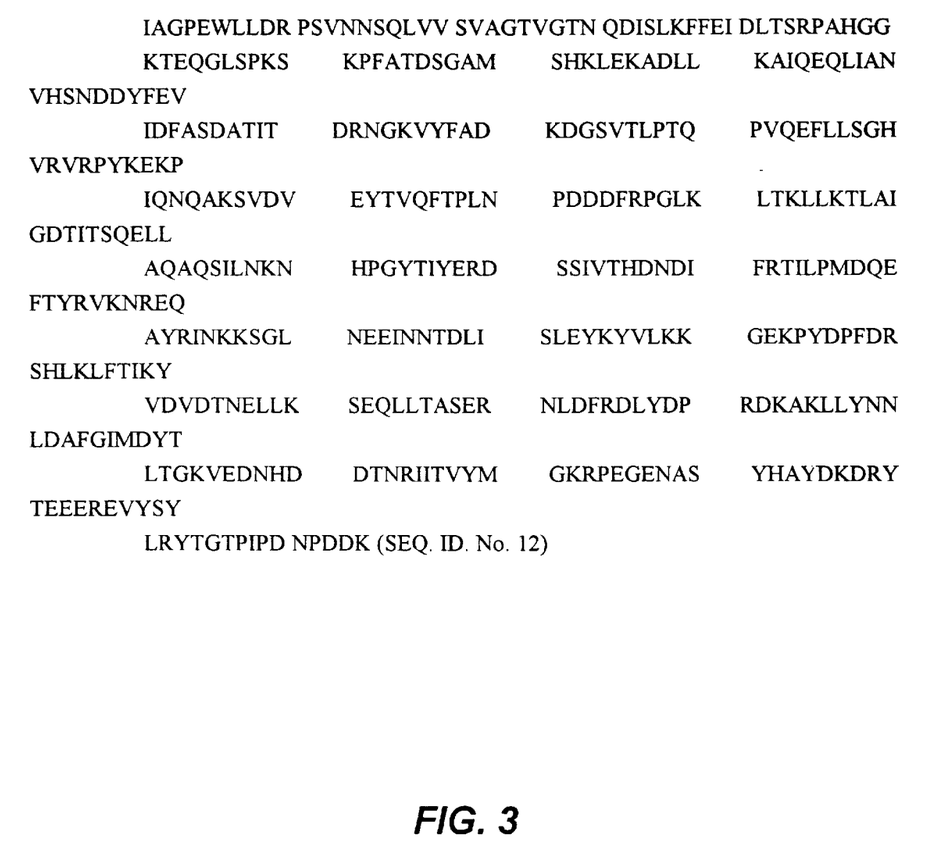
FIG. 3 is a representative amino acid sequence of streptokinase as described in K. W. Jackson and J. Tang, *Biochemistry* 21:6620–6625, 1982. A=alanine; C=cysteine; D=aspartic acid; E=glutamic acid; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; Y=tyrosine.

As noted above the peptides of the present invention are derived from streptokinase (available from ICN, Inc., Costa Mesa, Calif., No. 101114) (FIG. 3) and identified by their ability to ameliorate cell death. In the context of the present invention, the term "streptokinase" includes any analogues, homologues, mutants, isomers, or derivatives in addition to the naturally occurring molecule. The term "derived" refers to construction of a peptide based on the knowledge of the streptokinase sequence using any one of several suitable means, including, by way of example, isolation or synthesis.

Peptides of the present invention may be synthesized using any one of several means, including tea-bag methodology or solid phase peptide synthesis procedures described by Merrifield et al. (*Biochemistry* 21:5020–31, 1982) and Houghten (*Proc. Nat'l. Acad. Sci. (USA)* 82:5131–35, 1985), or using a commercially available automated synthesizer, such as the Applied Biosystems 430 A Peptide Synthesizer.

Alternatively, suitable peptides may be isolated from streptokinase by digestion of the molecule using any suitable means including, by way of example, a protease including plasminogen, trypsin, urokinase, enterokinase, pepsin, papain, and staphylococcus aureus protease ("SAP"), or any combination thereof. Preferably, streptokinase is digested with plasminogen.

Suitable peptides prepared by either of the means described above may be purified using any one of several suitable means, including affinity columns, salt precipitations, anion/cation exchange columns, sizing columns, and gel electrophoresis based on size and charge. Preferably, purification is accomplished using reverse-phase high pressure liquid chromatography (HPLC).

Suitable peptides prepared as described above may be assayed using any one of several suitable means of identifying their ability to ameliorate cell death, including culturing three separate biological preparations: (1) and (2) are cultured for a period of time and under suitable conditions to induce apoptosis; and (3) is cultured as a control group. Apoptosis can be induced by any one of several means, including chemotherapeutic agents, hypoosmotic shock, ultraviolet radiation, gamma-radiation, soft beta-radiation, serum deprivation or specific receptor mediated agents. Preferably, apoptosis is induced using ammonium persulfate which induces oxidative damage and, ultimately, results in cell death.

The peptide to be screened is administered to either biological preparation (1) or (2), and the percent cell death ascertained in all three biological preparations using, for example, trypan blue exclusion. The success of the peptide, for example if added to biological preparation (1), can be gauged by comparison with the cell death in biological preparations (2) and (3). Generally, a 50%–80% decrease in cell death and, preferably, a greater than 80% decrease, over biological preparation (2), is the indicia of a successful peptide. Even more preferably, a greater than 95% decrease in cell death is the indicia of a successful peptide. Alternatively, a method such as that disclosed in WO 94/25621, may be suitable for screening the compounds of the present invention.

Suitable peptides may be analyzed by any one of several means to ascertain their composition, including, by way of example, amino acid analysis (e.g., R. L. Heinriksen and S.

C. Meredith, *Anal. Biochem.* 160:65–74, 1984) after gas phase hydrolysis (N. M. Meltzer et al., *Anal. Biochem.* 160:356–61, 1987). The sequence of the streptokinase peptide may be confirmed by Edman degradation on a commercially available sequencer (e.g., R. M. Hewick et al., *J Biol. Chem.* 15:7990–8005, 1981).

In a preferred embodiment of the present invention, suitable peptides are of the following amino acid sequences:

a.  SER-VAL-ASP-VAL-GLU-TYR                                                             (SEQ. ID. No. 1)

b.  TYR-VAL-ASP-VAL-ASP-THR                                                             (SEQ. ID. No. 2)

c.  THR-VAL-ASP-VAL-GLU-TYR                                                             (SEQ. ID. No. 3)

d.  TYR-VAL-ASP-VAL-ASP-THR-ASN-GLU-LEU-LEU-LYS                                         (SEQ. ID. No. 4)

e.  SER-VAL-ASP-VAL-GLU-TYR-THR-VAL-GLN-PHE-THR-PRO-LEU-ASN-PRO-ASP-ASP-ASP            (SEQ. ID. No. 5)

f.  SER-VAL-ASP-VAL-GLU-TYR-THR-GLN-PHE-THR-ASP-PHE-ARG-GLY-LYS-LEU-THR-LYS-LEU-LEU    (SEQ. ID. No. 6)

g.  SER-VAL-ASP-VAL-GLU-TYR-THR-VAL-GLN-PHE-THR-PRO-LEU-ASN-PRO-ASP-ASP-ASP-PHE-ARG-PRO (SEQ. ID. No. 7)

h.  TYR-VAL-ASP-VAL-ASP-THR-ASN-GLU-LEU-LEU-LYS-SER-GLU-GLN-LEU-LEU-THR-ALA-SER-GLU    (SEQ. ID. No. 8)

In the context of the present invention, the term "peptide" includes analogues and fragments thereof. The term "analogue" refers to any derivative of the peptide and peptides in which one or more amino acids have been replaced with amino acids of similar size and charge, i.e., interchanging LEU and ILE or the attachment of another structure such as a cyclic compound or other molecule to the "peptide." The term "fragment" refers to any fragment of the peptide which is capable of ameliorating cell death as described above. Preferably, fragments are at least four amino acids in length; even more preferably, fragments are at least six amino acids in length.

Another aspect of the present invention provides polynucleotides which encode the above described peptides, analogues or fragments thereof. Polynucleotides and analogues thereof include, by way of example, RNA, DNA analogues thereof, including chimerics and PNA. The polynucleotides of the present invention may be synthesized or isolated. Synthesis may be accomplished using any one of several means including standard polynucleotide synthesis procedures. The polynucleotides coding for the aforementioned peptides could either be inserted into a standard plasmid or viral vector, introduced into bacterial or eukaryotic cells and the peptides of the present invention expressed and isolated.

Expression of the inserted polynucleotide can be determined in vitro using any one of the techniques described above. Expression of the inserted polynucleotide can be determined in vivo using any one of several methods, including, by way of example, immunofluorescence using a fluoresceinated ligand.

The sequences, constructs, vectors and other materials comprising the present invention can advantageously be in the enriched or isolated form. Within the context of the present invention, "enriched" means that the concentration of the material is at least about 2, 3, 4, 10, 100, or 1000 times its natural concentration, for example, advantageously 0.01% by weight, preferably at least about 0.1% by weight. Enriched preparations of about 0.5%, 1%, 5%, 10%, and 20%, by weight, are also contemplated.

Within the context of the present invention, the term "isolated" requires that the material be removed from its original environment (e.g., the natural environment if it is naturally occurring). For example, a naturally occurring oligonucleotide or peptide present in a living animal is not "isolated," but the same oligonucleotide or peptide, separated from some or all of the coexisting materials in the natural system, is "isolated."

Another aspect of the present invention provides constructs including one or more of the polynucleotides, as broadly described above. The constructs comprise a vector, such as a plasmid or viral expression vector, into which a polynucleotide of the present invention has been inserted, in either a sense or antisense orientation. Preferably, the construct further contains regulatory regions, including, for example, a promoter, operably linked to the polynucleotide. Large numbers of suitable vectors and promoters are known and are commercially available. The following expression vectors are provided by way of example: Prokaryotic: pBC, pBluescript SK, pBK, pNH8a, pNH16a, pNH18a, pNH46a, pCR-SCRIPT (Stratagene), ptrc99A, pKK223-3, pKK233-3, pDR540, pRIT5 (Pharmacia). Eukaryotic: TBK, pSV2cat, pOG44, pOG45, pXT1, pMClneo, pMClneo Poly A, pSG, pSG5 (Stratagene), pSVK3, pBPV, pMSG, pSVL (Pharmacia). Viral: retroviral, adenoviral and vaccinia virus.

Promoter regions may be selected from any desired gene using chloramphenicol transferase ("CAT") vectors or other vectors with selectable markers. Two appropriate vectors are pKK232-8 and pCM7. Particular named bacterial promoters include lac, lacz, T3, T7, gpt, lambda PRO and trc. Eukaryotic promoters include CMV immediate early, HSV thymidine kinase, early and late SV40, LTRs from retrovirus and mouse metallothionein-I. Selection of the appropriate vector and promoter is well within the level of one of ordinary skill in the art.

In a further embodiment, the present invention provides host cells containing the above-described construct. The host cell can be a eukaryotic cell, for example, a mammalian cell or a yeast cell; or a prokaryotic cell, such as a bacterial cell. Introduction of the construct into the host cell can be affected using any one of several methods known in the art, including by calcium phosphate transfection, DEAE, dextran mediated transfection, infection, or electroporation, as described in detail in, e.g., Davis et al., *Basic Methods of Molecular Biology,* 1986.

Constructs in host cells can be used in a conventional manner to produce the peptides coded by the polynucleotides, as described above, or the host cells can be administered directly to an animal in need thereof, as described below. Alternatively, the encoded peptide can be synthetically produced by conventional peptide synthesizers.

Pharmaceutical compositions containing the peptide, fragments or analogues thereof, or associated polynucleotides and constructs thereof (hereinafter referred to as "the compounds of the present invention") in an admixture with a pharmaceutical carrier or diluent can be prepared according to conventional pharmaceutical compounding techniques. Administration should account for the possibility of degradation of compounds of the present invention. The carrier may take a wide variety of forms depending on the form of preparation desired for administration, e.g., intravenous, oral, topical, aerosol, suppository, parenteral or spinal injection. Preferably, the peptide is administered directly to the targeted site, i.e., by stereotactic injection or other suitable means.

Pharmaceutical composition containing the peptide, fragment or analogues thereof or polynucleotides and constructs thereof may be combined with agent or drug that inhibits or delays or retards the metabolism/degradation of the peptide, fragments or analogues.

If necessary, the pharmaceutical preparations can be subjected to conventional pharmaceutical adjuvants such as preserving agents, stabilizing agents, wetting agents, salts for varying the osmotic pressure, and the like. The present pharmaceutical preparations may also contain other therapeutically valuable substances.

Within this embodiment of the present invention, the compounds of the present invention may be delivered using a suitable liposome delivery system, including, by way of example, those described in U.S. Pat. Nos. 4,241,046; 4,235,871; 4,394,448; 4,483,929; 4,745,074; 4,766,046; 4,873,088; 5,077,057; 5,180,713; and 5,277,914; or in Rahman et al., *J. of Liposome Research* 4:167–192, 1994.

Compounds of the present invention may also be delivered by chronic infusion using any suitable method known in the art, including an osmotic minipump (Alza Corp.) or delivery through a time release or sustained release medium. Suitable time release or sustained release systems include any methods known in the art, including media such as Elvax (or see, for example, U.S. Pat. Nos. 5,015,479, 4,088,798, 4,178,361, and 4,145,408). When using chronic infusion, time release, or sustained release mechanisms, the composition may be stereotactically injected orally, parenterally, or intramuscularly.

When polynucleotides of the present invention or constructs thereof are transfected or infected into a mammalian host cell, the mammalian cells may be administered to the patient in need thereof by any method known in the art, including that outlined in U.S. Pat. No. 5,082,670.

In another aspect of the present invention, the compositions of the present invention are utilized to treat diseases and conditions related to aging, cellular differentiation, and physical insult. These conditions and diseases include, by way of example, viral disorders, degenerative disorders, immune disorders, aging, cardiovascular disorders, and neoplastic disorders.

In one embodiment of this aspect of the present invention, compositions of the present invention (as described above) are administered to treat a warm-blooded animal suffering from or susceptible to a viral disorder. The association of cell death with a particular viral disorder may be determined by standard means. Such viral disorders include, by way of example, hepatitis, retroviral infections, and viral encephalitis, and AIDS/IIIV (Fauci, A. S., *Science* 262:1011, 1993; Ameisen, J. C., *Immunol. Today* 13:388, 1992; Gorla, R. et al., *AIDS Research and Human Retroviruses* 10(9):1097).

Compounds of the present invention may also be administered to treat a warm-blooded animal suffering from, or susceptible to, a neurodegenerative disorder. The association of cell death with a particular neurodegenerative disorder may be determined by establishing, for example, indicators of defects of neurologic function. Such neurodegenerative disorders include, by way of example, Parkinson's disease, (Beal, M. F. et al., *TINS* 16(4):125, 1993; Bloem, B. R. et al., *J Neurol. Sci.* 97:293 1990; Brennan, W. A. et al., *J. Neurochem.* 44:1948, 1985); Alzheimer's disease, (Beal, M. F. et al., *TINS 16*(4):125, 1993, Beal, M. F., *Ann. Neurol.* 31:119, 1992); Huntington's disease, (Beal, M. F. et al. *TINS* 16(4):125, 1993; Bloem, B. R. et al., *J. Neuro. Sci.* 97:293 1990; Brennan, W. A. et al., *J. Neurochem.* 44:1948, 1985); cerebellar degenerations, (Beal, M. F. et al., *TINS* 16(4):125, 1993); and, familial amyotrophic lateral sclerosis (FALS) (Olanow, C. W., *TINS* 16:439, 1993).

Compounds of the present invention may also be administered to treat a warm-blooded animal suffering from, or susceptible to, a cardiovascular disease. The association of cell death with a particular cardiovascular disease may be determined by any suitable means including microscopy of trypan blue exclusion or histologic features of all necrosis. Such cardiovascular diseases include, by way of example, atherosclerosis, myocardial infarction, heart failure, cardiomyopathy, myocardial reperfusion injury, and hypertensive heart disease.

Compounds of the present invention may also be administered to treat a warm-blooded animal suffering from, or susceptible to, autoimmune disease. The association of cell death with a particular autoimmune disorder may be determined, for example, by biochemical tests such as antibodies to virus or anti-DNA antibodies, microscopic appearance of blood cells and histologic appearance of affected tissue. Such immune diseases include, by way of example, AIDS/HIV, autoimmune disease and immune deficiencies. Autoimmune diseases include rheumatoid artlritis, systemic lupus erythematosus, insulin-dependent diabetes mellitus, lupus, pernicious anemia, dermatomyositis, enythema nodosum, Sjögren's syndrome, temporal arteritis, myasthenia gravis, Wegener's granulomatosis, glomerulonephritis, anti-phospholipid syndrome, and autoimmune polyarthritides. The connection between apoptosis and autoimmune disease has been documented in WO 94/08454.

Compounds of the present invention may also be administered to treat a warm-blooded animal suffering from, or susceptible to, a ncoplastic disorder. The association of cell death with a particular neoplastic disorder may be determined by, for example, microscopic examination of blood elements, histologic appearance of tissue, and genetic testing of tissue and blood-formed elements. Such neoplastic disorders include, by way of example, leukemia, sarcomas, myelomas, carcinomas, neuromas, melanoma, cancers of the breast, brain, colon, cervix, and prostrate, Hodgkin's disease, and non-Hodgkin's lymphoma.

Compounds of the present invention may also be administered to treat a warm-blooded animal suffering from, or susceptible to, an inflammatory disorder. The association of cell death with a particular inflammatory disorder may be determined by, for example, x-ray examination, blood tests such as, but not restricted to, rheumatoid factor and histologic appearance of tissue. Such inflammatory disorders include, by way of example, inflammatory joint disorders such as arthritis and inflammatory induced cell damage to the eye, brain, and other organs.

Compounds of the present invention may also be administered to treat a warm-blooded animal which has been subjected to physical insult. The term "physical insult" refers to injury resulting from sudden or severe shock, for example, from physical trauma, anoxia, hyperthermia, hypothermia, chemically induced damage, and trauma to the brain, spinal cord, kidney, heart, lungs, liver, skin and any other organ of the body.

Compounds of the present invention may also be administered to treat a warm-blooded animal suffering from such conditions as ischemia or reperfusion injury of various body organs, including, but not limited to, myocardial ischemia and reperfusion injury. renal ischemia, brain ischemia and/or reperfusion injury, spinal cord ischemia or reperfusion injury, retinal ischemia or infarction, and stroke.

Compounds of the present invention may also be administered to treat a warm-blooded animal suffering from such toxic insult as liver toxicity, pulmonary toxicity, and toxic damage to other body organs from chemicals, radiation and other noxious substances.

Compounds of the present invention may also be administered to treat a warm-blooded animal suffering from such conditions as macular degeneration, cataract formation, pancreatitis, Crohn's disease, ulcerative colitis and accelerated aging.

Compounds of the present invention may also be administered to treat a warm-blooded animal suffering from spinal cord disease, such as motor neuron diseases degeneration of spinal cord, Guillan Bare Syndrome, and demyelinating disease.

Compounds of the present invention may also be administered to treat a warm-blooded animal which has been subjected to a procedure with which cell death is associated. This association is determined by clinical examination and appropriate testing, depending on the organ. By way of example, heart requires echocardiograms, electrocardiograms, nuclear studies, and biochemical tests, e.g., CK, CK-MB, etc. Such procedures include, by way of example, bypass surgery, chemotherapy, and chemically-induced reperfusion.

Compounds of the present invention may also be administered to treat a warm-blooded animal which has been administered therapeutics which subject the animal to oxidative stress. The free radical production associated with oxidative stress may be identified and evaluated to ascertain the effect of the therapeutics using any suitable method, including thiobarbaturic acid colormetric assays (TBARS). Such therapeutics include, by way of example, clozapine, AZT, and anthracyclines.

Compounds of the present invention may also be administered to a biological preparation. In the context of the present invention, the term "biological preparation" refers to an ex vivo cell culture.

The compounds of the present invention or any combination thereof are administered in a therapeutically effective amount. A therapeutically effective amount is that amount sufficient to reduce cell death. A therapeutically effective amount can be determined by in vitro experiment followed by in vivo studies. The optimal dosage is that which produces maximal improvement with tolerated side effects. The optimal dosage is determined empirically and balances the benefits and adverse side effects.

The term "treatment" as used within the context of the present invention, refers to reducing or alleviating symptoms in a subject, preventing symptoms from worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. An unbalanced state disorder is "treated" by partially or wholly remedying the imbalance which causes the disorder or which makes it more severe.

A disorder is "treated" by partially or wholly remedying the deficiency which causes the disorder or which makes it more severe. For example, a disorder such as myocardial infarction is considered to be treated if administration of the composition provided herein (i) improves survival, (ii) results in fewer morbid events from the complications of myocardial infarction (e.g., heart failure and arrhythmias), or (iii) there is evidence of a lesser amount of damage to the heart due to a myocardial infarction (e.g., as assessed by the release of creatine kinase or imaging of the heart).

The following examples are provided by way of illustration, and not by way of limitation.

EXAMPLES

Example 1

Amelioration of Cell Death in Cardiac Myocytes

This example serves to demonstrate an assay useful to test peptides for their ability to ameliorate cell death.

Cardiac myocytes from embryonic chick hearts were grown in culture using the procedures described in Rabkin, Exper. *Cell. Res.* 188:262–266, 1990. Briefly, white Leghorn eggs were incubated in an automatic incubator (March Rollex, Calif., USA) for 7 days at 37.8° C. and 87% humidity. Hearts were then isolated under sterile conditions from the 7-day chick embryo. Blood and connective tissue were removed under a dissecting microscope in a solution of balanced salts (DMS8) with the following composition (mM): NaCl 116, KCl 5.4, $NaH_2PO_4$ 1 and dextrose 5.6. Disaggregation was carried out by 5-minute digestions in 0.005% trypsin (Gibco Laboratories, Burlington, Ontario), 0.1% BSA and $1\times10^7$ DNAse per mL, DMS8 (Worthington Biochemicals, Frederic, N.J., USA) at 37° C. After three digestions, the digests were diluted 1:5 in culture medium and the cells centrifuged for three minutes at 1000 g and plated.

The cultured cardiac myocytes were incubated with 1 mM ammonium persulfate for 2 hours at 37° C. to induce oxidative damage. Cell viability was assessed by Trypan blue exclusion. Six samples containing cells were then incubated with 0.0, 0.000375, 0.00375, 0.0375, 0.375 and 37.5 μM streptokinase (Hoechts-Roussel Pharmaceuticals), respectively, and 0.0, 0.000246, 0.00246, 0.0246, 0.246 and 24.6 μM plasminogen, respectively (see Table 1), for 1–2 hours at 37° C. and assessed by Trypan blue exclusion.

Control cell samples were treated with 1 mM ammonium persulfate in the absence of streptokinase (STK) and plasminogen under the same conditions.

The results are described in Table 1 in terms of the percent cell death induced by ammonium persulfate. The data represents the mean of six (6) duplicate determinations, none of which differed by more than 5%.

TABLE 1

| Streptokinase (μM) | Plasminogen (μM) | Cell Death (%) |
|---|---|---|
| 0 (Control) | 0 (Control) | 81 |
| 0.000375 | 0.000246 | 50 |
| 0.00375 | 0.00246 | 37 |
| 0.0375 | 0.0246 | 29 |
| 0.375 | 0.246 | 25 |
| 37.5 | 24.6 | 16 |

Example 2

Separation of Streptokinase Fragments by Reverse Phase HPLC

This example serves to demonstrate the isolation of peptides derived from streptokinase and their ability to ameliorate cell death in cardiac myocytes.

Streptokinase was incubated with plasminogen at a 1:1 molar concentration for 1–2 hours at 37° C. Streptokinase and plasminogen fragments were subsequently separated using a reverse phase phenyl HPLC column (Waters) and a linear gradient of 1%/min and an isopropanol gradient in 0.1 ammonium bicarbonate buffer, pH 6.5.

Each of the nineteen (19) resulting fractions was tested for the peptide's ability to ameliorate cell death according to the assay described in Example 1. The results of this assay are presented in Table 2. The data in Table 2 represent the mean of duplicate determinations. None of the determinations differed by more than 5%.

TABLE 2

| Fraction Number | Cell Death (%) |
|---|---|
| 1 | 87 |
| 2 | 79 |
| 3 | 79 |
| 4 | 62 |
| 5 | 83 |
| 6 | 77 |
| 7 | 81 |
| 8 | 79 |
| 9 | 82 |
| 10 | 63 |
| 11 | 78 |
| 12 | 29 |
| 13 | 39 |
| 14 | 80 |
| 15 | 76 |
| 16 | 63 |
| 17 | 79 |
| 18 | 74 |
| 19 | 77 |

The HPLC-purified peptides eluted in fractions 12 and 13 were analyzed by amino acid analysis (R. L. Heinriksen and S. C. Meredith, *Anal. Biochem.* 160:65–74, 1984). after gas phase sequencing (N. M. Meltzer et al., *Anal. Biochem.* 160:356–61, 1987). The sequence of the purified peptide was determined by Edman degradation on a commercially available sequencer (R. M. Hewick et al., *J. Biol. Chem.* 15:7990–8005, 1981). The sequences were:

fraction 12: YVDVDTNELLKSEQLLTASE (SEQ. ID NO. 8)
fraction 13: SVDVEYTVQFTPLNPDDDFRP (SEQ. ID NO. 7)

Example 3

Amelioration of Cell Death by Synthesized Peptides

This example serves to demonstrate the suitability of specific peptides in amelioration of cell death.

Based on the sequences identified in Example 2, peptides were synthesized using a commercially available automated synthesizer (Applied Biosystems 430 A Peptide Synthesizer), purified by and tested according to the assay described in Example 1 for their ability to ameliorate cell death in cardiac myocytes. The sequences for these peptides were:

| | |
|---|---|
| 6mer #1: | SVDVEY (SEQ. ID NO. 1) |
| 6mer #2: | YVDVDT (SEQ. ID NO. 2) |
| 6mer #3: | TVDVEY (SEQ. ID NO. 3) |
| 11mer: | YVDVDTNELLK (SEQ. ID NO. 4) |
| 18mer: | SVDVEYTVQFTPLNPDDD (SEQ. ID NO. 5) |
| 20mer: | SVDVEYTQFTDFRGKLTKLL (SEQ. ID NO. 6) |
| fraction 12: | YVDVDTNELLKSEQLLTASE (SEQ. ID NO. 8) |
| fraction 13: | SVDVEYTVQFTPLNPDDDFRP (SEQ. ID NO. 7) |
| Irrelevant #1: | NFLRGKLKLYTGEACRTGDR (SEQ. ID NO. 9) |
| Irrelevant #2: | RLILDSRVLERYLLEAKEAE (SEQ. ID NO. 10) |
| Irrelevant #3: | EVTEEEETVPLKTLE-AMIDE (SEQ. ID NO. 11) |

Table 3 presents the percentage of dead cells as measured by Trypan blue assessment as described in Example 1. The data in Table 3 represents means of duplicate determinations, which did not differ by more than 5%.

TABLE 3

| | Peptide Concentration (μM): | | | | |
|---|---|---|---|---|---|
| Peptide | 0 | 5 | 10 | 15 | 20 |
| 20mer | 80.3 | 47.6 | 35.4 | 31.6 | 23.1 |
| 6mer #1 | 82.4 | 51.9 | — | — | 36.8 |
| 6mer #2 | 82.4 | 37.0 | — | — | 25.4 |
| 6mer #3 | — | — | — | — | — |
| 11mer | 80.7 | 38.6 | — | — | — |
| 18mer | 84.5 | — | — | — | 54.4 |
| Irrelevant #1 | 79.6 | 77.1 | — | — | 67.6 |
| Irrelevant #2 | 79.6 | 77.4 | — | — | 76.1 |
| Irrelevant #3 | 79.6 | 79.5 | — | — | 81.1 |

These peptides effectively protect cells against cell death in the low micromolar range and exhibit a good dose-response relationship. The highest concentration of the 20mer peptide (SEQ. ID NO. 6) was able to reduce the number of dead cells to the 20% range, despite the presence of agents designed to induce cell death. This is comparable to cell death observed under control conditions (i.e., in the absence of ammonium persulfate). Three irrelevant peptides of different sequences, but approximately the same length, utilized as negative controls, did not show any significant effect on cell viability in this assay.

Example 4

Amelioration of Cell Death in Isolated Intact Rat Heart

This example serves to demonstrate the ability of the peptides of the present invention to ameliorate cell death in the heart.

Rats weighing between 0.3 and 0.4 kilograms were injected with heparin and then 1 hr. later killed by cervical fracture. Their hearts were immediately excised and placed in an oxygenated Krebs-Henseleit solution of the following composition (in millimole/liter): NaCl, 119.9; KCl, 6.0; NaHCO$_3$, 25.0; MgSO$_4$, 1.2; CaCl$_2$, 1.6; KH$_2$PO$_4$, 1.2; and glucose, 10.0. The aorta was cannulated and the heart was perfused with oxygenated Krebs-Henseleit solution, using the Lanngendorff technique at a constant flow of 15 ml per minute with a diastolic perfusion pressure greater than 50 mm Hg. The perfusate was previously equilibrated and constantly aerated with 95% 0$_2$ and 5% CO$_2$. The right ventricle was stimulated with square waves of 1 V for 1 ms every 500 ms (Pulsar 61 stimulator, Frederick Haer & Co., Brunswick, Maine).

Following a 30 min. equilibration, the left atrium was incised to permit the insertion into the left ventricle of a balloon-tipped catheter which was inflated at a resting pressure of 20 mm Hg. Left ventricular pressure was measured using a statham pressure transducer (Gould P230 ID) and recorded on a Gould polygraph (Model 2900, Gould, Cleveland, Ohio).

The preparation was allowed to stabilize for 30 min. prior to commencement of the experimental protocol. After obtaining baseline measurements, myocardial ischemia was produced by decreasing the perfusate flow to 2.5 ml per minute (80% of control) and by using an anoxic solution (95% N$_2$ and 5% CO$_2$). The period of ischemia and hypoxia (hereinafter referred to as "the ischemic period") lasted 45 minutes. Perfusion rate and oxygenation were then returned to control levels. Left ventricular pressure measurements were recorded before, during, and for 120 min. after myocardial ischemia.

Figure 1:
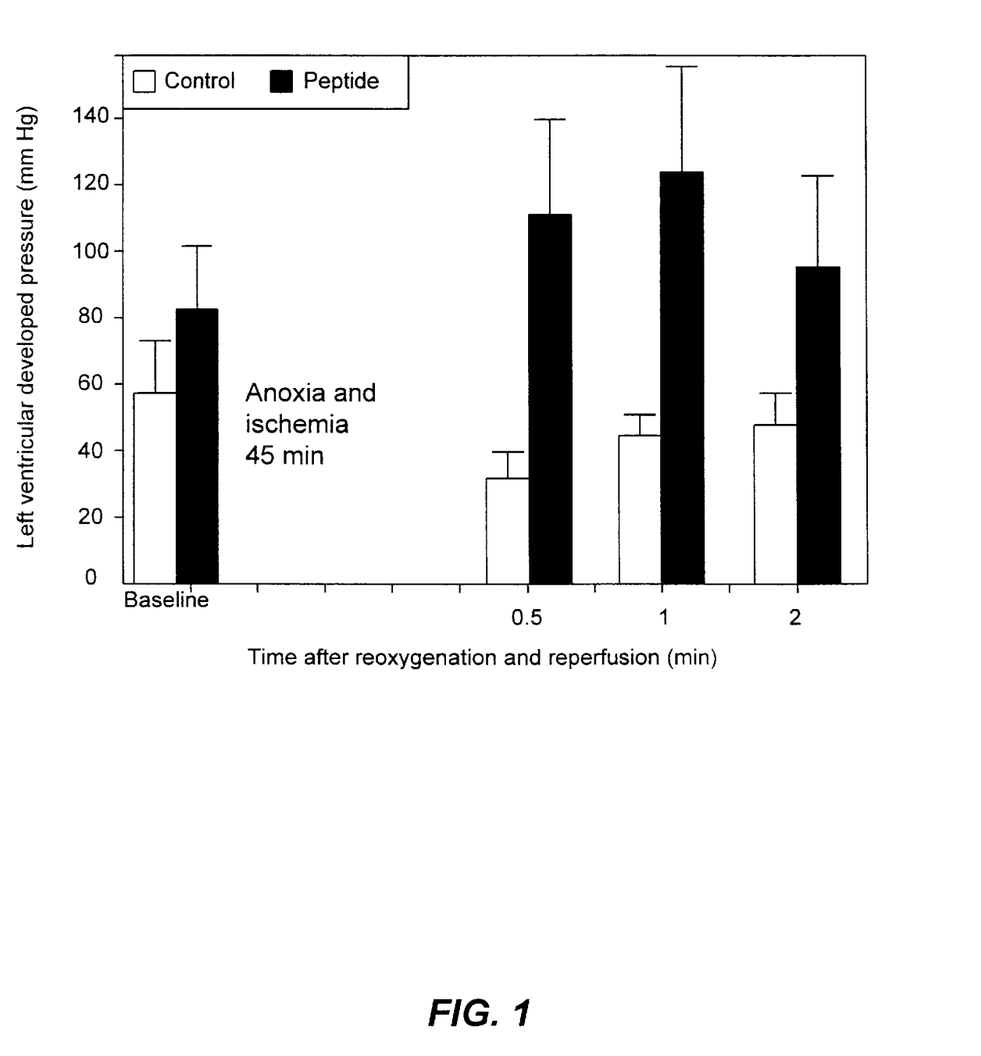
FIG. 1 is a bar graph which depicts left ventricular developed pressure, i.e., the difference between peak systolic pressure and resting left ventricular pressure, in the isolated rat heart that was exposed to 45 minutes of ischemia by subjecting the heart to an 80% reduction in perfusion flow rate, under anoxic conditions (85% $N_2$ and 5% $CO_2$), followed by reperfusion at 15 ml/min. and reoxygenation. There is a more rapid recovery in the hearts that received the peptide (20 mer) (SEQ. ID. No. 6) prior to reperfusion.

One group of isolated rat hearts was pretreated with a 20mer (SEQ. ID NO. 6). The 20mer (SEQ. ID NO. 6) was added to the perfusate and hearts were perfused starting 15 minutes before reperfusion and continuing for 5–10 minutes after reperfusion. Left ventricular developed pressure was measured and compared to a control group of isolated rat hearts receiving no pretreatment. Left ventricular developed pressure, an index of left ventricular performance, is the difference between peak systolic pressure and resting left ventricular pressure. The results of this experiment are plotted in FIG. 1. Hearts pretreated with the 20mer peptide (SEQ. ID NO. 6) experienced a rapid recovery.

Example 5

Amelioration of Cell Death in Spinal Cord Cells

This example serves to demonstrate the effectiveness of the peptides of the present invention to ameliorate neuronal cell death. Spinal cord cells isolated from embryonic chicks were grown in culture for 5–7 days. Chick spinal cord cells were cultured as described briefly as follows. Cell cultures were prepared from 7-day chick embryo. Ventral portions of spinal cord were dissected free of meninges and dorsal root ganglia and diced into small pieces in Dulbecco's phosphate-buffered saline (PBS). Tissue fragments were incubated in PBS with 0.25% trypsin and 20 ug/ml DNase for 30 min at 36° C. Trypsin was inactivated by the addition of horse serum and cells were dissociated by gentle pipetting.

Isolated cells were washed, resuspended in medium and plated onto plastic coverslips in petri dishes. The medium consisted of Eagle's minimum essential medium (MEM), 10% fetal bovine serum (FBS), 5 mg/ml D-glucose and 25 µg/ml gentamycin. Cells were grown in an incubator with 5% CO$_2$/95% air at 37° C. and the medium was renewed twice a week. Cells were used for experiment after 14 days.

Figure 2:
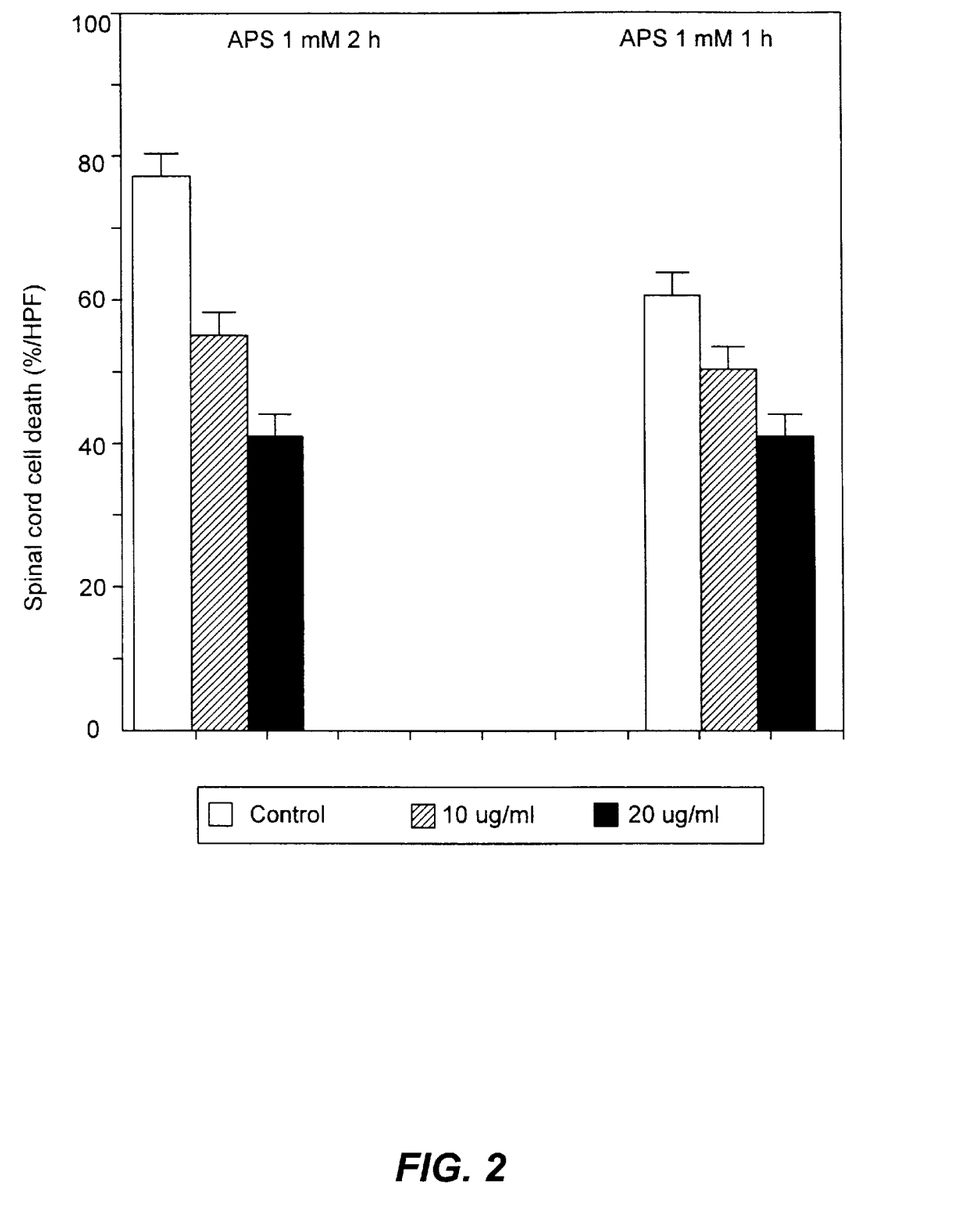
FIG. 2 is a bar graph which depicts survival of spinal cord cells exposed to ammonium persulfate, 1 mM for 2 hours (left) and for 1 hour (right). Cells pretreated with the 20mer (SEQ. ID. No. 6) had much better survival, i.e, less death. Indeed, the 20mer almost completely prevented cell death, compared to the number of dead cells observed in the absence of ammonium persulfate.

Both the experimental and control cultures were treated with 1 mM ammonium persulfate for 1 or 2 hours at 37° C. The experimental cultures were treated with either 10 µg/ml or 20 µg/ml of the 20mer peptide (SEQ. ID NO. 6) for the same length of time. Results of two experiments, each carried out in duplicate, are shown in FIG. 2. The number of dead cells, assayed by trypan blue, in the experimental groups was compared to that in the control group. Pretreatment with the 20mer peptide (SEQ. ID NO. 6) dramatically enhanced cell survival.

Example 6

Amelioration of Cell Death in Human Hematopoietic Cell Lines

This example serves to demonstrate the use of the compounds of the present invention in ameliorating serum-deprivation-induced cell death.

The hematopoietic, growth factor dependent cell lines, M07E and TF-1 (Mijajima, CDNAX Research Institute, Palo Alto, Calif.), were starved for 30 hours in DMEM containing 1% fetal calf serum (Hyclone, Logan, Utah) in the presence or absence of 20 µg/ml of the 20mer peptide (SEQ. ID NO. 6). Cell viability was measured by one of two methods, trypan blue exclusion or $^3$H-thymidine incorporation (Alai et al., *J. Biol. Chem.* 267:18021–18025, 1992).

Cells in the latter group were washed free of the 20mer (SEQ. ID NO. 6), given saturating concentrations of growth factor (5 ng/ml of human interleukin-3) and incubated for an additional 22 hours. After the 22 hours, 18 µCi of $^3$H-thymidine (2 Ci/mmol) was added and, after 2 hours, the cellular contents were harvested onto filtermats. Then $^3$H-thymidine incorporation was measured using an LKB Betaplate Harvester and liquid scintillation counter. The results of this experiment are presented in Tables 4 and 5. Note the increased viability of cells treated with the 20mer peptide (SEQ. ID NO. 6).

TABLE 4

Trypan Blue Counts (% viability)

| Cell Line | Control | 20 µg/ml 20mer Peptide |
|---|---|---|
| M07E | 11 ± 1% | 20 ± 0.5% |
| TF-1 | 6 ± 1% | 29 ± 1% |

TABLE 5

$^3$H-Thymidine Counts (counts per minute)

| Cell Line | Control | 20 µg/ml 20mer Peptide |
|---|---|---|
| M07E | 2,003 ± 468 | 4,282 ± 212 |
| TF-1 | 14,728 ± 2,825 | 32,701 ± 5,565 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated peptide of streptokinase, wherein said peptide ameliorates cell death when administered to a cell.

2. The isolated peptide according to claim 1 having the sequence as set forth in SEQ. ID. No. 1.

3. The isolated peptide according to claim 1 having the sequence as set forth in SEQ. ID. No. 2.

4. The isolated peptide according to claim 1 having the sequence as set forth in SEQ. ID. No. 3.

5. The isolated peptide according to claim 1 having the sequence as set forth in SEQ. ID. No. 4.

6. The isolated peptide according to claim 1 having the sequence as set forth in SEQ. ID. No. 5.

7. The isolated peptide according to claim 1 having the sequence as set forth in SEQ. ID. No. 6.

8. The isolated peptide according to claim 1 having the sequence as set forth in SEQ. ID. No. 7.

9. The isolated peptide according to claim 1 having the sequence as set forth in SEQ. No. 8.

10. An isolated nucleic acid segment which encodes a peptide according to any one of claims 1–9.

* * * * *